(12) United States Patent
Akagi et al.

(10) Patent No.: US 7,856,676 B2
(45) Date of Patent: Dec. 28, 2010

(54) CAPSULE-TYPE MEDICAL DEVICE COLLECTOR AND CAPSULE-TYPE MEDICAL DEVICE COLLECTING KIT

(75) Inventors: Toshimasa Akagi, Hachioji (JP); Masami Kurihara, Musashimurayama (JP)

(73) Assignee: Olympus Corporation, Tokyo (JP)

( * ) Notice: Subject to any disclaimer, the term of this patent is extended or adjusted under 35 U.S.C. 154(b) by 727 days.

(21) Appl. No.: 11/631,241

(22) PCT Filed: Aug. 23, 2005

(86) PCT No.: PCT/JP2005/015288
§ 371 (c)(1),
(2), (4) Date: Feb. 26, 2007

(87) PCT Pub. No.: WO2006/022268
PCT Pub. Date: Mar. 2, 2006

(65) Prior Publication Data
US 2007/0260204 A1 Nov. 8, 2007

(30) Foreign Application Priority Data
Aug. 23, 2004 (JP) .............................. 2004-242753

(51) Int. Cl.
*E03C 1/26* (2006.01)
*E03D 9/00* (2006.01)
*A61M 1/00* (2006.01)
*B01D 29/00* (2006.01)

(52) U.S. Cl. ............................... 4/290; 4/256.1; 4/661; 604/317; 210/238

(58) Field of Classification Search ................... 435/7.1; 206/569; 604/317; 4/290, 256.1, 66.1
See application file for complete search history.

(56) References Cited

U.S. PATENT DOCUMENTS
2,617,996 A * 11/1952 Hoffman et al. ............. 4/256.1
(Continued)

FOREIGN PATENT DOCUMENTS
JP 62-138759 6/1987
(Continued)

OTHER PUBLICATIONS
Japanese Office Action dated Jun. 22, 2010 with Partial English Translation.

*Primary Examiner*—Tatyana Zalukaeva
*Assistant Examiner*—Susan Su
(74) *Attorney, Agent, or Firm*—Scully, Scott, Murphy & Presser, P.C.

(57) ABSTRACT

A capsule-type medical device collector has a cylindrical net member (61*a*) whose mesh size is formed so as to be able to collect a capsule endoscope (3), slits 61*d* and (61*d*), an INSU-LOCK binder (61*e*), and handle members 61*f* and (61*f*). By binding the other end of the cylindrical net member (61*a*) with the INSULOCK binder (61*e*) to form the cylindrical net member (61*a*) in a bag shape and sandwiching ear members (61*a*1) and (61*a*1) of the cylindrical net member (61*a*) between a toilet stool (7) and a toilet seat (71), the cylindrical net member (61*a*) is fixed on the toilet stool (7). After excretion, the cylindrical net member (61*a*) is taken out and only a capsule endoscope (3) is collected. In such a manner, a capsule-type medical device discharged from a subject to the outside is easily collected.

7 Claims, 10 Drawing Sheets

U.S. PATENT DOCUMENTS

| | | | | |
|---|---|---|---|---|
| 3,346,883 | A * | 10/1967 | Ersek | 4/661 |
| 3,381,315 | A * | 5/1968 | Glassberg | 4/484 |
| 3,484,875 | A * | 12/1969 | Eisenberg | 4/484 |
| 3,540,433 | A * | 11/1970 | Brockman | 600/562 |
| 3,718,431 | A * | 2/1973 | Wild | 436/66 |
| 3,754,287 | A * | 8/1973 | Taylor | 4/661 |
| 3,860,971 | A * | 1/1975 | Dirks | 68/235 D |
| 4,309,782 | A | 1/1982 | Paulin | |
| 4,343,053 | A * | 8/1982 | O'Connor | 4/452 |
| 4,445,235 | A * | 5/1984 | Slover et al. | 4/144.2 |
| 5,316,386 | A * | 5/1994 | Moore | 383/10 |
| 5,412,819 | A * | 5/1995 | Matusewicz et al. | 4/661 |
| 5,463,782 | A * | 11/1995 | Carlson et al. | 4/661 |
| 5,704,349 | A * | 1/1998 | Hubbard et al. | 128/206.19 |
| 6,048,407 | A * | 4/2000 | Schoch | 134/6 |
| 6,112,339 | A * | 9/2000 | Nichols et al. | 4/484 |
| 6,116,780 | A * | 9/2000 | Young et al. | 383/44 |
| 6,210,573 | B1 * | 4/2001 | Marshall | 210/238 |
| 6,358,477 | B1 * | 3/2002 | Webb et al. | 422/102 |
| 6,415,455 | B1 * | 7/2002 | Slaon et al. | 4/315 |
| 6,434,762 | B2 * | 8/2002 | Gordon | 4/483 |
| 6,447,463 | B1 * | 9/2002 | Borkowski | 600/562 |
| 6,523,187 | B1 * | 2/2003 | Brink et al. | 4/484 |
| 6,532,605 | B1 * | 3/2003 | Howell | 4/484 |
| 6,612,741 | B1 * | 9/2003 | Horne | 383/43 |
| 6,625,823 | B1 * | 9/2003 | Abbott | 4/484 |
| 6,640,355 | B1 * | 11/2003 | Samide | 4/661 |
| 6,857,819 | B2 * | 2/2005 | Gunderson, III | 405/60 |
| 6,922,852 | B1 * | 8/2005 | Blum | 4/144.4 |
| 2001/0034904 | A1 * | 11/2001 | Phillips et al. | 4/484 |
| 2004/0175289 | A1 | 9/2004 | Takizawa et al. | |
| 2004/0176735 | A1 * | 9/2004 | Snell | 604/385.01 |
| 2004/0231689 | A1 * | 11/2004 | Kobayashi et al. | 132/222 |
| 2005/0264016 | A1 * | 12/2005 | Davis | 294/1.3 |
| 2007/0066865 | A1 * | 3/2007 | Fukuda et al. | 600/102 |
| 2008/0220513 | A1 * | 9/2008 | Bucci | 435/290.1 |

FOREIGN PATENT DOCUMENTS

| | | |
|---|---|---|
| JP | 63-216563 | 9/1988 |
| JP | 2003-19111 | 1/2003 |
| JP | 2003-260026 | 9/2003 |
| JP | 2004-267350 | 9/2004 |
| WO | WO 02/102243 A1 | 12/2002 |
| WO | WO 2004/045374 A3 | 6/2004 |

* cited by examiner

CAPSULE-TYPE MEDICAL DEVICE COLLECTOR AND CAPSULE-TYPE MEDICAL DEVICE COLLECTING KIT

TECHNICAL FIELD

The present invention relates to a capsule-type medical device collector and a capsule-type medical device collecting kit for collecting a device introduced to the inside of the subject, for example, a swallowable capsule-type medical device (capsule endoscope).

BACKGROUND ART

In recent years, in the field of an endoscope, a capsule endoscope having the image capturing function and the radio communication function has appeared. The capsule endoscope is swallowed from the mouth of a subject (human body) for observation (examination) and travels in organs such as the stomach and small intestine (in the body cavity) with the peristaltic movement of the organs while sequentially capturing images by using the image capturing function for an observation period until the capsule endoscope is naturally discharged from the living body of the subject.

Image data captured in the body cavity by the capsule endoscope for the observation period in which the capsule endoscope travels in the organs is sequentially transmitted to the outside of the subject by the radio communication function such as Bluetooth and housed in a memory provided in an external receiving device. By carrying the receiving device having the radio communication function and a memory function, the subject can freely move even in the observation period since the subject swallows the capsule endoscope until the capsule endoscope is discharged. After the observation, a doctor or a nurse performs a diagnosis by displaying images in the body cavity on display means such as a display on the basis of the image data housed in the memory of the receiving device.

Generally, a plurality of antenna elements for receiving image signals transmitted from the capsule endoscope are disposed so as to spread on the outside of the subject, and the receiving device receives image data by selecting one of the antenna elements, with small reception error in the image signals by switching the plurality of antenna elements. Patent Document 1 describes a receiving device for detecting the position of a capsule endoscope in the subject as a transmission source of image signals on the basis of field intensities of antenna elements while switching the antenna elements. The antenna elements are provided with adhesive and are adhered on predetermined regions of the surface of the subject. The antenna element is usually constructed by an antenna body and a coaxial cable bonded and electrically connected to the antenna body.

Patent Document 1: Japanese Patent Application Laid-Open No. 2003-19111

DISCLOSURE OF INVENTION

Problem to be Solved by the Invention

In recent years, for example, a capsule endoscope that extracts body fluid or detects pH in an organ has been devised. Such a capsule endoscope has to be collected after a test is finished and the capsule endoscope is discharged to the outside of the subject, and the result has to be observed. However, a particular collecting device solving a problem of how to collect a discharged capsule endoscope has not been conventionally provided.

The present invention has been achieved in consideration of the above problem and an object of the invention is to provide a capsule-type medical device collector and a capsule-type medical device collecting kit capable of easily collecting a capsule-type medical device discharged from the subject to the outside.

Means for Solving Problem

A capsule-type medical device collector according to one aspect of the present invention includes a cylindrical net member which is formed in a cylindrical shape and whose mesh size can collect a capsule-type medical device; a slit having predetermined length and extended from one end of the cylindrical net member in a longitudinal direction; and a binding member for binding the other end of the cylindrical net member to form the cylindrical net member in a bag shape.

The capsule-type medical device collector may further include handle members provided at one end of the cylindrical net member so as to face each other.

In the capsule-type medical device collector, the cylindrical net member may have a pair of ear members to make the cylindrical net member open by the slit, and the cylindrical net member can be held by sandwiching the ear members between a toilet stool and a toilet seat.

In the capsule-type medical device collector, the cylindrical net member may be formed in a flat cylinder having a flat part and a folded part, and the slit may be formed so as to cut in a longitudinal direction from a center portion of one end of the flat part.

In the capsule-type medical device collector, the handle member may be provided at an end of each of the ear members.

A capsule-type medical device collecting kit according to another aspect of the present invention includes a capsule-type medical device collector including, a cylindrical net member which is formed in a cylindrical shape and whose mesh size can collect a capsule-type medical device, a slit having a predetermined length and extended from one end of the cylindrical net member in a longitudinal direction, and a binding member for binding the other end of the cylindrical net member to form the cylindrical net member in a bag shape; a sleeve member having a cylindrical shape in which the capsule-type medical device collector can be inserted; gloves and a mask for a work of collecting the capsule-type medical device; and a collection bag for housing the capsule-type medical device collector, the sleeve member, the gloves, and the mask.

The capsule-type medical device collecting kit may further include a housing bag for housing the capsule-type medical device collected by the capsule-type medical device collector.

In the capsule-type medical device collecting kit, the capsule-type medical device collector may further include handle members provided at one end of the cylindrical net member so as to face each other.

In the capsule-type medical device collecting kit, the cylindrical net member may have a pair of ear members to make the cylindrical net member open by the slit, and the cylindrical net member can be held by sandwiching the ear members between a toilet stool and a toilet seat.

In the capsule-type medical device collecting kit, the cylindrical net member may be formed in a flat cylinder having a flat part and a folded part, and the slit may be formed so as to cut in a longitudinal direction from a center portion of one end of the flat part.

In the capsule-type medical device collecting kit, the handle member may be provided at an end of each of the ear members.

Effect of the Invention

The capsule-type medical device collector according to the present invention has a cylindrical net member whose mesh size is formed so as to be able to collect a capsule-type medical device, slits, a binding member, and handle members. By binding the other end of the cylindrical net member with the binding member, the cylindrical net member is formed in a bag shape. The cylindrical net member is mounted so as to be sandwiched between a toilet stool and a toilet seat. With the configuration, an effect such that a capsule-type medical device discharged from a subject to the outside can be easily collected is produced.

In the capsule-type medical device collecting kit according to the invention, the capsule-type medical device collector whose cylindrical net member is formed in a bag shape by the binding member is mounted on a toilet stool, and the capsule-type medical device is collected together with excrement discharged from the subject by the cylindrical net member. In such a manner, the capsule-type medical device discharged from the subject to the outside can be easily collected. By using the gloves and the mask for collecting work, the cylindrical net member is inserted through the cylindrical sleeve member, and the subject squeezes the cylindrical net member over the sleeve member. Consequently, an effect such that the capsule-type medical device can be easily found and taken out is attained.

EXPLANATIONS OF LETTERS OR NUMERALS

Figure 1:
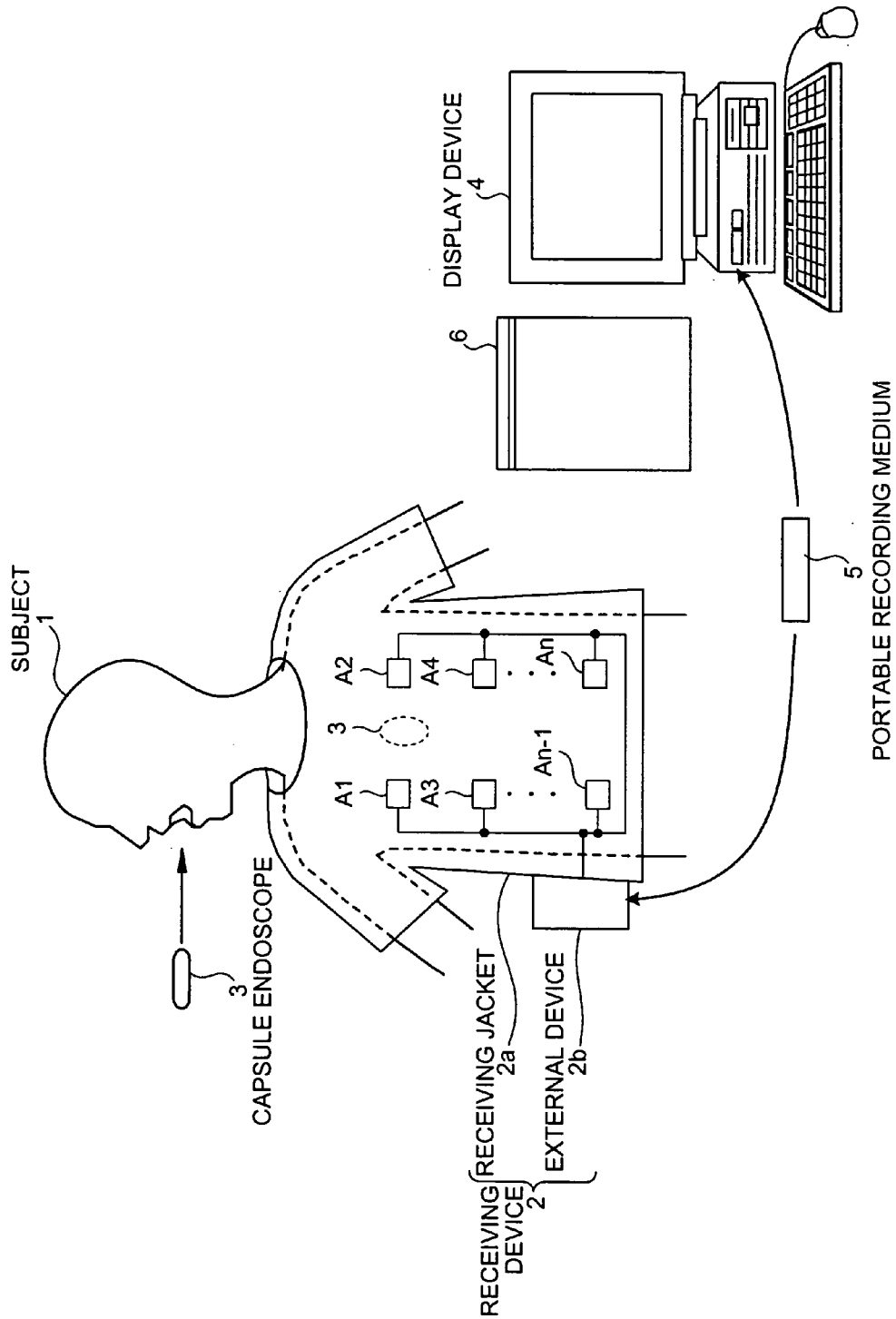
FIG. 1 is a schematic diagram showing a general configuration of a wireless in-vivo information acquiring system having a capsule-type medical device collecting kit according to the present invention.

1 Subject
2 Receiving device
2a Receiving jacket
2b External device
3 Capsule endoscope
4 Display
5 Portable recording medium
6 Capsule-type medical device collecting kit
7 Toilet stool
61 Capsule-type medical device collector
61a Cylindrical net member
61a1 Ear member
61b Flat part
61c Folded part
61d Slit
61e INSULOCK binder
61f Handle member
61f1 Tag
62 Sleeve member
63 Glove
64 Mask
65 Collection bag
65a Bottom face
65b, 67b, 68a Zipper
66 Manual
67 Housing bag
67a Space to be filled in
68 Kit bag
70 Cover
71 Toilet seat
72 Stopper

BEST MODE(S) FOR CARRYING OUT THE INVENTION

Embodiments of a capsule-type medical device collector and a capsule-type medical device collecting kit according to the present invention will be described in detail below with reference to FIGS. 1 to 22. The invention is not limited to the embodiments but can be variously modified without departing from the gist of the invention.

First Embodiment

FIG. 1 is a schematic diagram showing a general configuration of a wireless in-vivo information acquiring system having a capsule-type medical device collecting kit according to the invention. In FIG. 1, the wireless in-vivo information acquiring system has a receiving device 2 having the radio receiving function and a capsule endoscope (capsule-type medical device) 3 introduced in a subject 1, capturing a body cavity image, and transmitting data such as an image signal to the receiving device 2. The wireless in-vivo information acquiring system also has a display device 4 for displaying a body cavity image on the basis of the image signal received by the receiving device 2, and a portable recording medium 5 for exchange of data between the receiving device 2 and the display device 4. The wireless in-vivo information acquiring system also has a capsule-type medical device collecting kit 6 for collecting the capsule endoscope 3 discharged to the outside of the subject 1 after completion of the examination.

The receiving device 2 has a receiving jacket 2a having a shape such that the subject 1 can wear it and having reception antennae A1 to An, and an external device 2b for processing radio signals received via the receiving jacket 2a and the like. The subject 1 carries both of the receiving jacket 2a and the external device 2b. The reception antennae A1 to An may be directly adhered to the outer surface of the subject 1 and may not be provided for the receiving jacket 2a. The reception antennae A1 to An which can be detachably attached to the receiving jacket 2a may be also used.

The capsule endoscope 3 has a front end cover having a not-shown semi-sphere dome shape, a trunk cover in which a cylindrical trunk and a rear end having an almost semi-sphere dome shape are integrally formed, and function executing means housed in the trunk cover. By joining a joint part of the front end cover and a joint part of the trunk cover, a capsule-shaped medical device formed in swallowable shape and fluid-tightly sealed is obtained. The capsule endoscope 3 has therein, for example, a cell such as a button cell. By supplying power from the cell, the function executing means for executing predetermined functions such as illuminating function, image capturing function, radio function, body fluid extracting function, and pH detecting function is driven, and capturing of body cavity images and data transmission of an image signal or the like to the receiving device 2 and the like is performed.

The display device 4 is provided to display a body cavity image and the like captured by the capsule endoscope 3, and has a configuration such as a workstation for displaying an image on the basis of data obtained by the portable recording medium 5. Concretely, the display device 4 may have a configuration of directly displaying an image by a CRT display, a liquid crystal display, or the like and outputting an image to another medium such as a printer or the like.

The portable recording medium 5 has a structure which is removably inserted to the external device 2b and the display device 4 and can output or record information when inserted in the external device 2b and the display device 4. In the embodiment, while the capsule endoscope 3 travels in the body cavity of the subject 1, the portable recording medium 5 is inserted in the external device 2b and records data transmitted from the capsule endoscope 3. After the capsule endoscope 3 is discharged from the subject 1, that is, after image capturing in the subject 1 is finished, the capsule endoscope 3 is taken out from the external device 2b and inserted in the display device 4. The data recorded in the portable recording medium 5 is read by the display device 4. For example, by performing exchange of data between the external device 2b and the display 4 by the portable recording medium 5 such as a CompactFlash® memory, the subject 1 can move more freely during capturing of images in the body cavity as compared with the case where the external device 2b and the display device 4 are directly connected to each other via a wire. Although the portable recording medium 5 is used for exchange of data between the external device 2b and the display device 4 in the embodiment, the present invention is not limited to the case. For example, another built-in recording device such as a hard disk may be used as the external device 2b. For exchange of data with the display device 4, the recording device and the display device 4 may be connected to each other with a wire or wirelessly.

Figure 2:
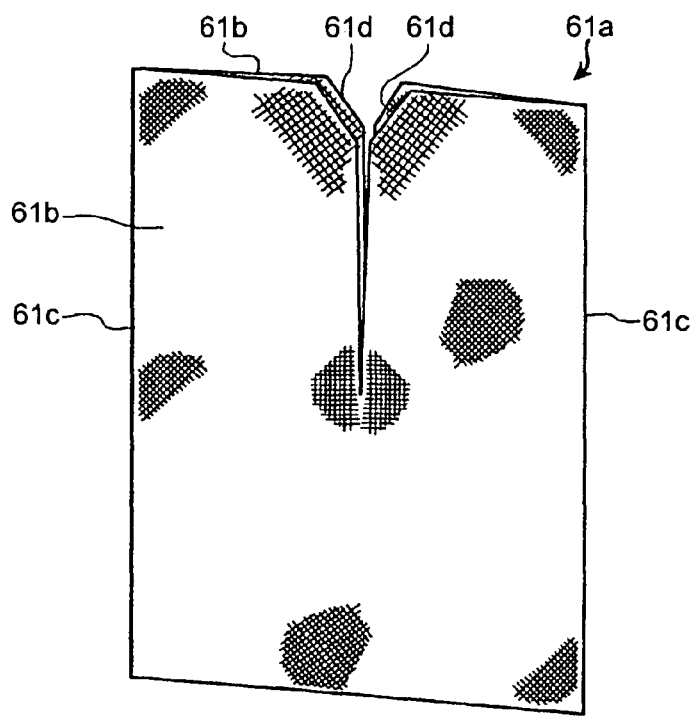
FIG. 2 is a perspective view of a cylindrical net member of a capsule-type medical device collector as a component of the capsule-type medical device collecting kit shown in FIG. 1.
Figure 3:
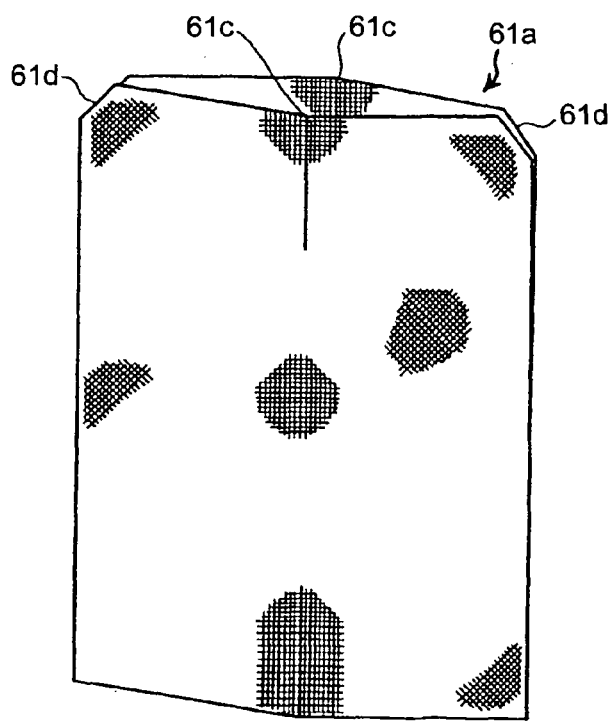
FIG. 3 is a perspective view showing a deformation state of the cylindrical net member.

FIGS. 2 to 11 are perspective views showing components of the capsule-type medical device collecting kit. FIGS. 2 and 3 are perspective views of a cylindrical net member. FIGS. 4 to 11 are perspective views showing the capsule-type medical device collector, a sleeve member, gloves, a mask, a collection bag, a manual, a housing bag, and a state where the capsule endoscope is housed in the housing bag, respectively.

In FIGS. 2 to 11, the capsule-type medical device collecting kit 6 is constructed by a capsule-type medical device collector 61 constructed by using a cylindrical net member 61a as a body, a sleeve member 62 in which the capsule-type medical device collector 61 is inserted, gloves 63 for a collecting work, a mask 64 for the collecting work, and a collection bag 65 for collecting the components of the collecting kit 6. In addition, the capsule-type medical device collecting kit 6 may include a manual 66 in which the procedure of collecting work is written, a housing bag 67 housing the capsule endoscope, and a kit bag 68 in which the collection bag 65 is housed. Preferably, the components of the capsule-type medical device collection kit 6 are made of a material having, for example, flexibility so that they can be folded or compactly packed.

As the cylindrical net member 61a, a net woven material (cylindrical net member) is used, which is obtained by performing annealing as fabrication on a net woven material (rod-shaped net member) obtained by weaving stretched filament formed by stretching molding or a rod-shaped net member formed by resin integral extrusion molding. The cylindrical net member 61a of the embodiment is formed in a flat cylindrical shape having flat parts 61b and 61b opposed to each other and folded parts 61c and 61c opposed to each other as shown in FIG. 2. V-shaped slits 61d and 61d extend so as to have a predetermined length in the longitudinal direction, which is about the half of the length of the cylindrical net member 61a from almost the center of one end (upper end in the longitudinal direction in FIG. 2) of the flat parts 61b and 61b. In the embodiment, when one end of the cylindrical net member 61a is opened along the slits 61d and 61d, a pair of ear members 61a1 and 61a1 is formed. For example, in the case of mounting the capsule-type medical device collector 61 on a toilet with a bidet function, a water discharge nozzle of the bidet which comes forward from the toilet rear side (water tank side) moves in a V-shaped notched space formed by the V-shaped slits 61d and 61d. With the configuration, the contact between the cylindrical net member 61a and the water discharge nozzle can be avoided, and breakage, failure, or the like of the water discharge nozzle can be prevented.

Figure 4:
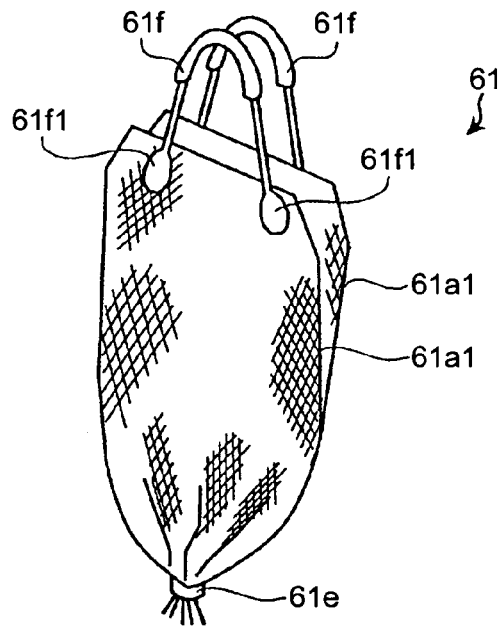
FIG. 4 is a perspective view showing the configuration of a capsule-type medical device collector.

The cylindrical net member 61a is stretched so that, as shown in FIG. 3, the folded parts 61c are positioned almost in the center of the flat parts, and is deformed so that the extension line of each of the slits 61d in the longitudinal direction serves as a folded part. In the deformed state, the other end (the end on the bottom side in the longitudinal direction in FIG. 3) is, for example, fan-folded from the folded part after the deformation. As shown in FIG. 4, the portion is bundled with an INSULOCK (which is binding band) 61e as a binding member, thereby forming the cylindrical net member 61a in a bag shape. In such a manner, the capsule-type medical device collector 61 is constructed. When the cylindrical net member 61a is formed in a bag shape in a deformed state, because of the influence of the mark of the folded part 61c, the cylindrical net member 61a can be formed in a bag shape in which the space is created.

The deforming process can be performed by a mechanical process. Preferably, by forming, for example, bending tendency of a hat in the cylindrical net member 61a by using a mold or the like, a bag shape in which the space is created in the net member can be easily maintained.

The capsule-type medical device collector 61 has handle members 61f and 61f provided at the ends of ear members 61a1 and 61a1 (upper ends in the longitudinal direction in FIG. 4). The handle members 61f and 61f are, for example, constructed of a snap-fit structure with a hinge portion from polyethylene like as the handles for typical paper bags. The handle members 61f have tags 61f1 and 61f1 at both ends. By retaining the tags 61f1 and 61f1 by two meshes in the ear members 61a1, an arch-shaped handle is formed. The cylindrical net member 61a is made from, for example, a net made of polyethylene material. The meshes of the net are formed in a size that the capsule endoscope 3 can be collected and excrement from the subject 1 can be removed.

As the cylindrical net member, for example, a net formed by weaving strings or a sink-corner strainer made by a polypropylene film can be used. As a weaving method, for example, circular weaving can be used to form a cylinder like seamless stocking. A cylindrical net member having a configuration in which a number of circular holes are opened in a polyethylene film may be used. The binding portion may be bound by heat welding or bonding in place of an INSULOCK binder. Further, the cylindrical net member and the handle member can be also manufactured by integral molding.

Figure 5:
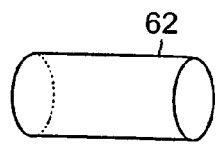
FIG. 5 is a perspective view of a sleeve member.
Figure 6:
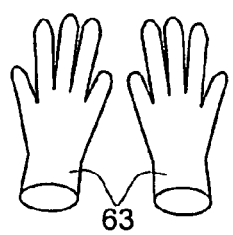
FIG. 6 is a perspective view of gloves.
Figure 7:
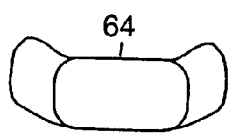
FIG. 7 is a perspective view of a mask.
Figure 8:
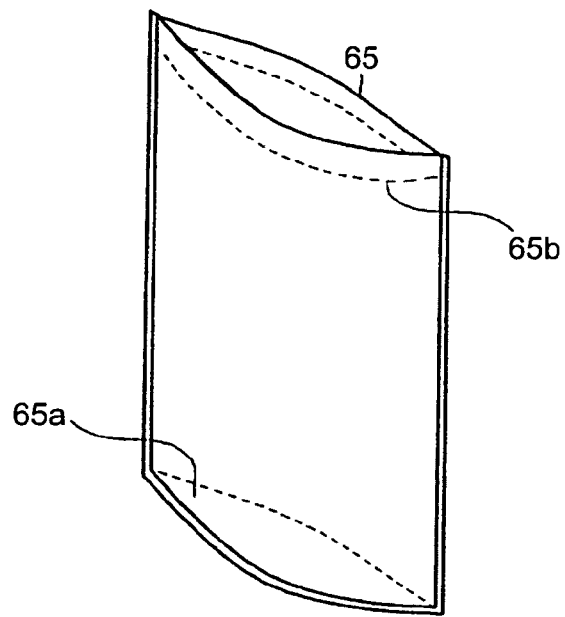
FIG. 8 is a perspective view of a collection bag.
Figure 9:
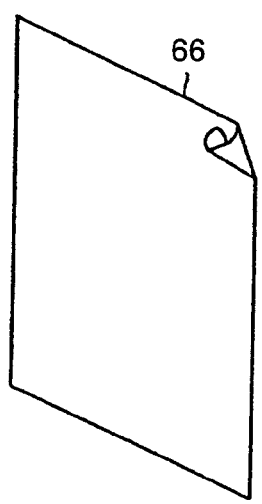
FIG. 9 is a perspective view of a manual.

As shown in FIG. 5, the sleeve member 62 is formed in a hollow cylindrical shape so that the cylindrical net member 61a can be inserted therein. The sleeve member 62 is made of a flexible material such as polyethylene material, and has a structure that a work of squeezing the inserted cylindrical net member 61a from the outside without making the hands dirty can be easily performed. The sleeve member can be constructed by a cardboard tube or a plastic ring.

The gloves 63 and the mask 64 for the collecting work are formed of a polyethylene material of a simple type provided as a countermeasure against dirt and bad smell. The gloves 63 and the mask 64 may be discarded after the collecting work of the capsule endoscope 3.

The collection bag 65 is a bag in which the capsule-type medical device collector 61, the sleeve member 62, the gloves 63, the mask 64, and the other dirty things (for example, used tissue paper) are housed after the collecting work of the capsule endoscope 3. The collection bag 65 is made of, for example, nylon polyethylene laminate material and formed by aluminum evaporation using, for example, an aluminum bag with zipper seal so that the collection bag 65 is not transparent, and a bottom face 65a is provided at the bottom. The bottom face 65a is folded before use. When the bag is open, the bottom face 65a is unfolded and functions as a bottom face, thereby enabling the collection bag 65 to be held in an upright state. A zipper 65b is provided at the upper end opening of the collection bag 65 and enables the opening to be closed after putting the dirty things and enables the closed state to be held, thereby preventing generation of bad odor. Also, dirty things cannot be seen, thereby enabling confidential information of the subject or the like to be kept.

Figure 10:
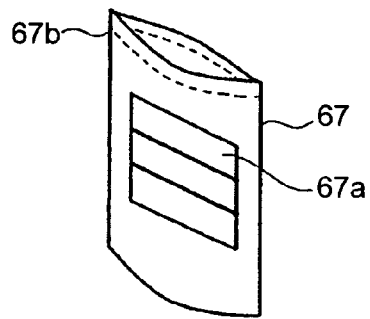
FIG. 10 is a perspective view of a housing bag.
Figure 11:
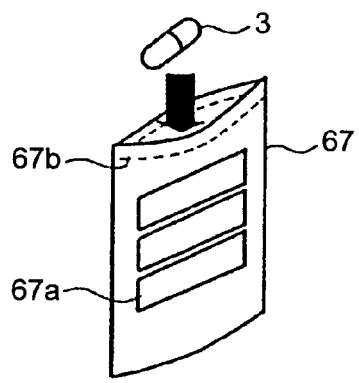
FIG. 11 is a perspective view showing a state where the capsule endoscope is housed in the housing bag.

As shown in FIG. 10, the housing bag 67 is a bag for housing the capsule endoscope 3 collected by the capsule-type medical device collector 61 and has a space to be filled in 67a in which the name of the subject and the like can be written on the surface. The capsule endoscope 3 is housed in the housing bag 67 as shown in FIG. 11 and a zipper 67b provided at the upper end opening is closed, thereby preventing the collected capsule endoscope 3 from being lost. The collected capsule endoscope 3 may be housed in the collection bag 65 in a state where it is held in the capsule-type medical device collector 61. The housing bag 67 may not be housed in the collection bag 65 but may be kept on a tray or the like dedicated to keep only the housing bags 67 each housing the capsule endoscope 3.

Figure 12:
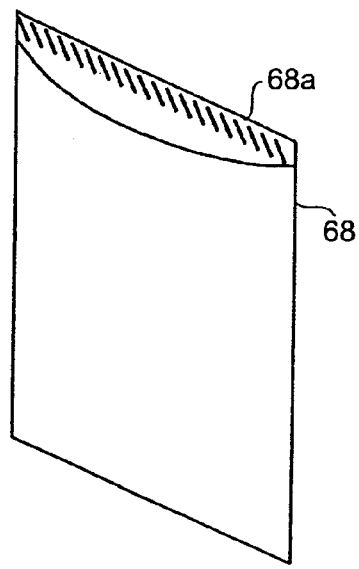
FIG. 12 is a perspective view of a kit bag.
Figure 13:
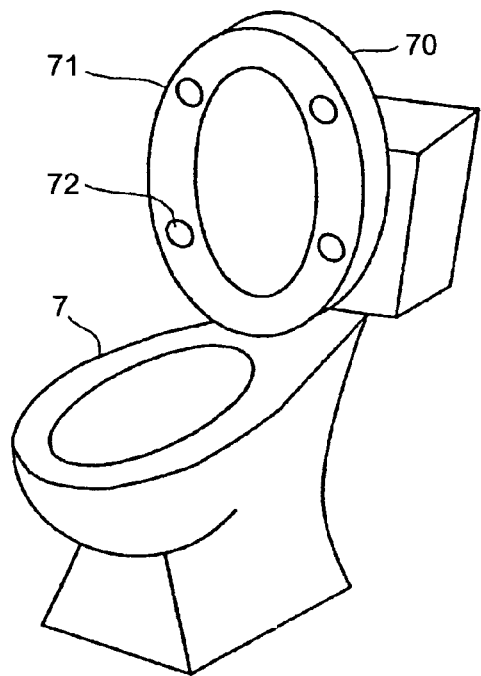
FIG. 13 is a perspective view of a toilet, for explaining the procedure of a work of collecting the capsule endoscope shown in FIG. 1.

As shown in FIG. 12, the kit bag 68 is provided to house the collection bag 65 and is made of a polyethylene material. An adhesive 68a is applied to an upper end opening portion. By housing the collection bag 65 in the kit bag 68, further cleanliness is obtained. The kit bag 68 can also serve as a packaging bag in which the components of the collection kit 6 can be housed together in an unused state.

Figure 14:
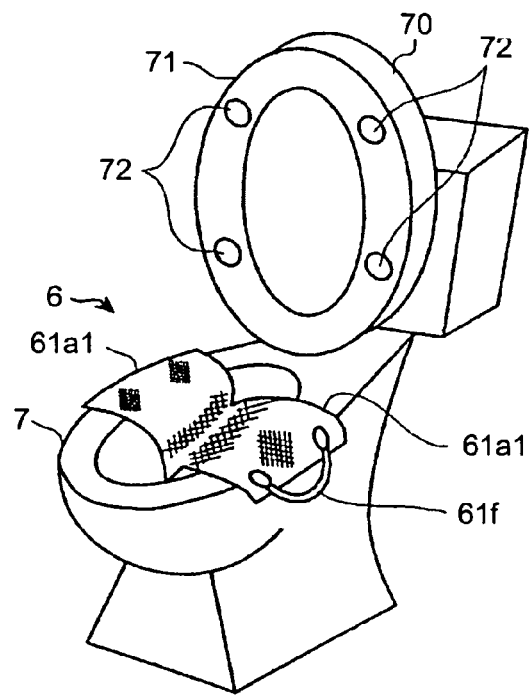
FIG. 14 is a perspective view of a toilet and a capsule-type medical device collector, for explaining the procedure of a work of collecting the capsule endoscope.
Figure 15:
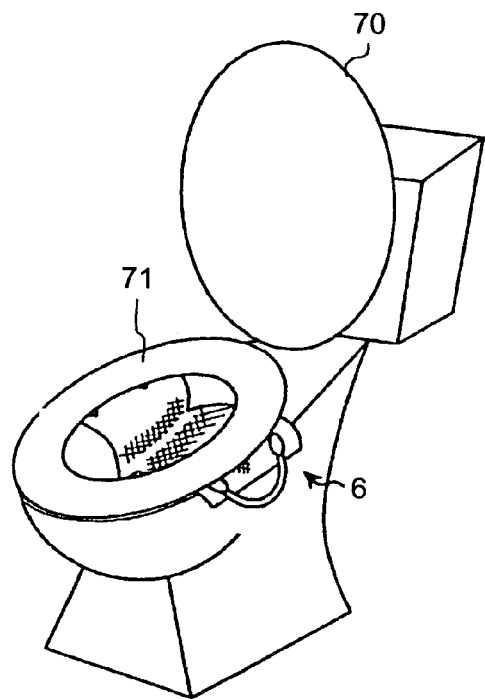
FIG. 15 is a perspective view of a toilet and a capsule-type medical device collector.

Next, the procedure of the work of collecting the capsule endoscope 3 will be described with reference to FIGS. 13 to 22. First, in FIG. 13, a cover 70 of a toilet stool 7 is opened and a toilet seat 71 is lifted. Next, as shown in FIG. 14, the cylindrical net member 61a of the capsule-type medical device collector 61 is unfolded and the ear members 61a1 and 61a1 are mounted on the toilet stool 7 so that the V-shaped slits 61d and 61d are positioned in the longitudinal direction of the toilet stool 7. The toilet seat is lowered so that the ear members 61a1 and 61a1 are sandwiched between the toilet stool 7 and stoppers 72 provided on the under face of the toilet seat 71 to fix the capsule-type medical device collector 61 (refer to FIG. 15). In such a manner, it is prepared for discharging operation of the capsule endoscope 3 of the subject.

Figure 16:
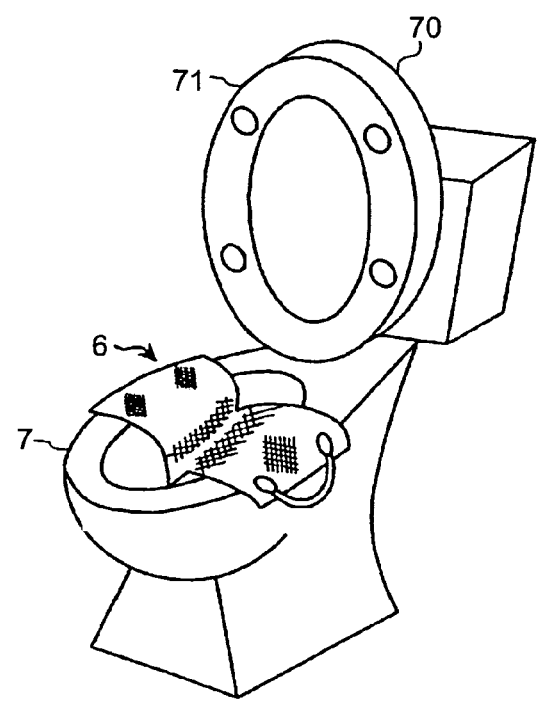
FIG. 16 is a perspective view of the toilet and the capsule-type medical device collector.
Figure 17:
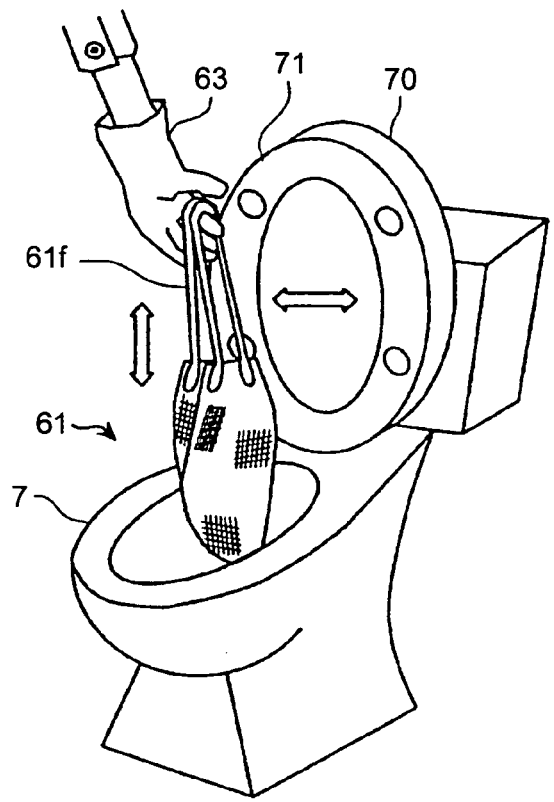
FIG. 17 is a perspective view of the toilet, the capsule-type medical device collector, and a glove.

After completion of the discharging operation of the subject, the toilet seat 71 is lifted up to cancel the state where the capsule-type medical device collector 61 is fixed (refer to FIG. 16). The subject puts on the gloves 63, grabs the handle members 61f, and moves the cylindrical net member 61a around, for example, about ten times in the water in the toilet stool 7, thereby removing the excrement (refer to FIG. 17). When used tissue paper or the like exists, it is held in the collection bag 65 which is preliminarily unfolded and held upright. If tissue paper is thrown into the toilet stool 7 and the toilet stool 7 is flushed with water immediately after discharge of the subject, the tissue paper may be caught by the cylindrical net member 61a, and it takes time to find the capsule endoscope 3. Preferably, such a cautionary statement is written in the manual 66.

Figure 18:
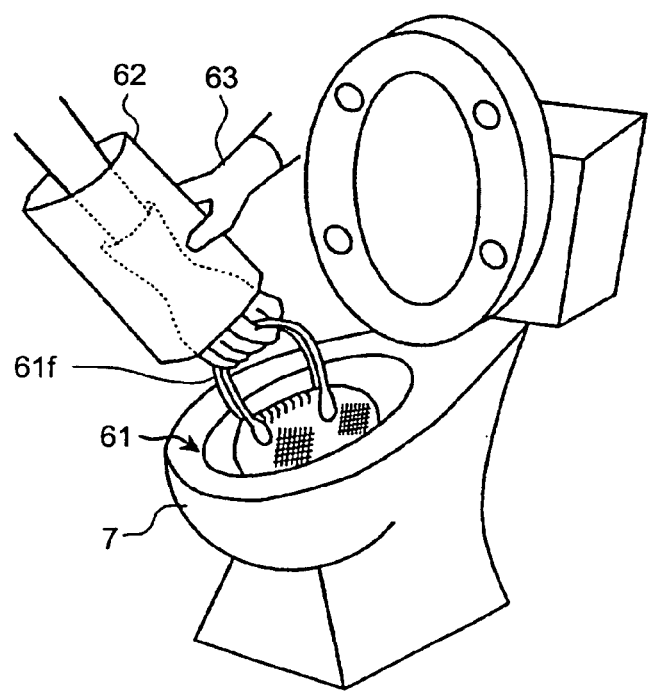
FIG. 18 is a perspective view of the toilet, the capsule-type medical device collector, a sleeve member, and the glove.
Figure 19:
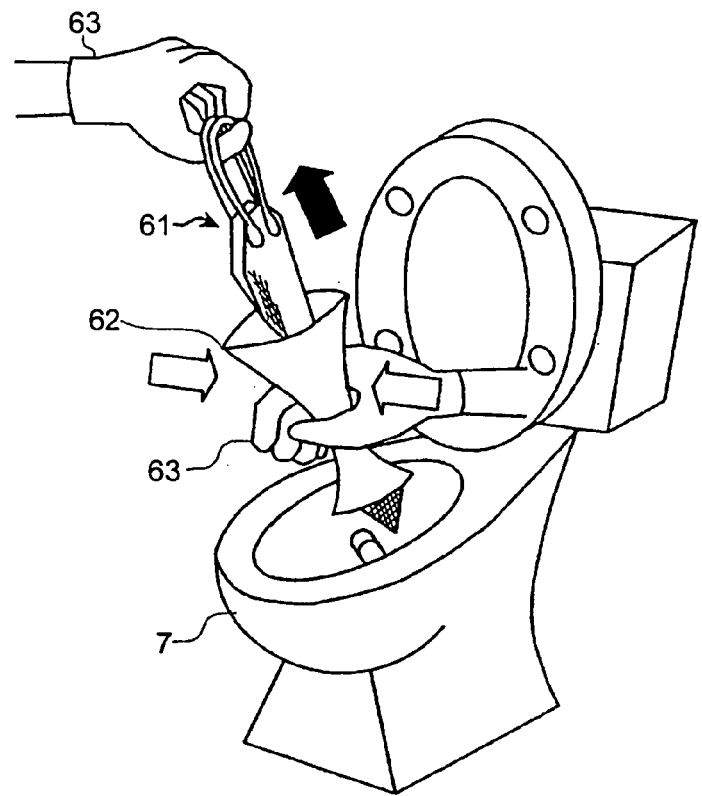
FIG. 19 is a perspective view of the toilet, the capsule-type medical device collector, the sleeve member, and the gloves.

At the time of washing out the excrement by water stream, there is the possibility that, depending on the hardness of the excrement, the excrement cannot be removed thoroughly and remains at the bottom or the like of the cylindrical net member 61a. As shown in FIG. 18, one of the hands, wearing the glove 63 and inserted through the sleeve member 62 grabs the handle member 61f, the other hand wearing the glove 63 holds the sleeve member 62, the one hand pulls the handle member 61f up from the toilet stool 7 so that the cylindrical net member 61a is inserted in the sleeve member 62. The other hand squeezes the bottom and the like of the cylindrical net member 61 over the sleeve member 62 to eliminate the remaining excrement (refer to FIG. 19).

Figure 20:
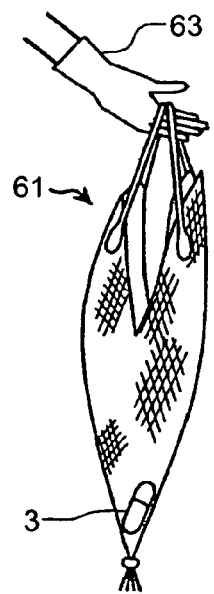
FIG. 20 is a perspective view of the capsule-type medical device collector and the glove.
Figure 21:
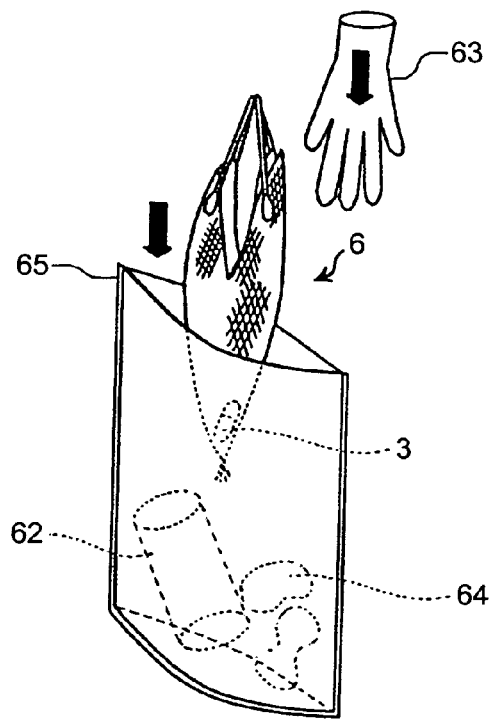
FIG. 21 is a perspective view of the capsule-type medical device collector, the sleeve member, the glove, and a collection bag.
Figure 22:
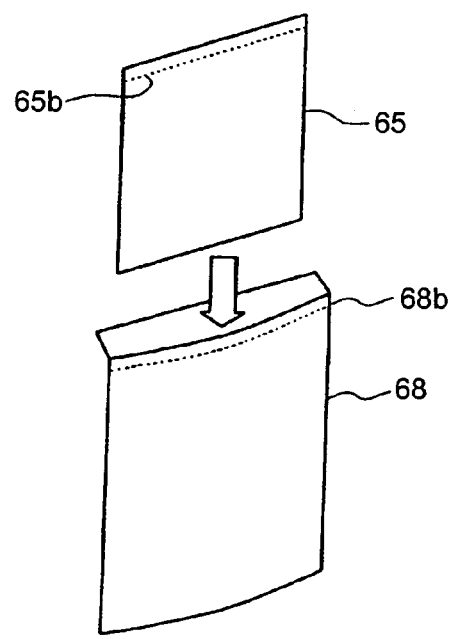
FIG. 22 is a perspective view of the collection bag and a kit bag.

By the operation, the excrement is removed from the cylindrical net member 61a, so that only the capsule endoscope 3 discharged together with excrement remains at the bottom of the cylindrical net member 61a (refer to FIG. 20). Next, the capsule-type medical device collector 61 (including the capsule endoscope 3), the sleeve member 62, the gloves 63, and the mask 64 used in the collecting work are put in the collection bag 65 (refer to FIG. 21), and the collection bag 65 is closed with the zipper 65b and is housed in the kit bag 68 (refer to FIG. 22). The kit bag 68 is hermetically closed with the zipper 68a. The collected capsule endoscope 3 can be taken out from the capsule-type medical device collector 61, housed in the housing 67, and kept on a dedicated tray or the like. By writing the name of the subject and the like in the space to be filled in in the housing bag 67, the subject is easily specified.

As described above, the bottom portion of the capsule-type medical device collector according to the embodiment is bound by an INSULOCK binder so as to be formed in a bag shape. The capsule-type medical device collector has a cylindrical net member whose mesh size can collect the capsule-type medical device. Since the cylindrical net member is mounted so as to be sandwiched between the toilet stool and the toilet seat, the capsule-type medical device discharged from the subject to the outside can be easily collected.

In the embodiment, the cylindrical net member is formed in a flat cylinder having flat parts and folded parts. The slits are formed so as to extend from a center portion of one end of each of the flat parts in the longitudinal direction. The cylindrical net member is deformed so that the folded parts are positioned in almost the center of the flat part and extend on the extension line in the longitudinal direction of the slits. By fan-folding the end, the cylindrical net member can be maintained in a bag shape more easily. Therefore, at the time of mounting the capsule-type medical device collector on the toilet stool, the cylindrical net member can cover the whole opening of the toilet sheet with the net by the maintained bag shape and the formed ear members. Irrespective of the position of the buttocks of the seated subject, the discharged capsule endoscope can be collected easily and reliably.

In the capsule-type medical device collecting kit according to the embodiment, the capsule-type medical device collector having the cylindrical net member formed in the bag shape is mounted on the toilet stool to house the capsule-type medical device discharged together with excretion by the cylindrical net member. Thus, the capsule-type medical device discharged from the subject to the outside can be easily collected. With the gloves for the collecting work, the mask, and the like, the cylindrical net member may be inserted in the sleeve member having a cylindrical shape, the subject squeezes the cylindrical net member over the sleeve member by his/her hand from the outside to remove excretion and take out only the capsule-type medical device. Thus, the capsule-type medical device can be easily found and taken out.

In the capsule-type medical device collecting kit of the embodiment, the capsule-type medical device collector in which the capsule-type medical device remains and the components (the gloves, the mask, and the like) of the collection kit used for the collecting work can be hermetically housed in the collection bag. Thus, bad smell and the like can be easily prevented.

The capsule-type medical device collector according to the invention is not limited to use for the above-described seat-type western toilet but can be also used for a Japanese-style toilet. In this case, the cylindrical net member is mounted on a Japanese-style toilet bowl. After that, the subject step on the ear members of the cylindrical net member with both feet, thereby enabling the capsule-type medical device collector to be fixed. Consequently, the capsule-type medical device can be easily collected.

INDUSTRIAL APPLICABILITY

As described above, the capsule-type medical device collector and the capsule-type medical device collecting kit according to the invention are useful for a medical observing device introduced in the human body to observe a region to be examined and, particularly suitable for easily collecting a capsule-type medical device discharged from the subject to the outside.

The invention claimed is:

1. A capsule-type medical device collecting kit, comprising:
   a capsule-type medical device collector having:
      a cylindrical net member disposed in a flat configuration such that there are two opposing flat parts and two opposing folded parts, the mesh size of the cylindrical net member being adapted for collecting a capsule-type medical device;
      a pair of slits having predetermined length, said slits extend longitudinally from an open end of the cylindrical net member, each slit being formed at the center of each of the two flat parts between the folded parts;
      a binding member that binds the other open end of the cylindrical net member to form the cylindrical net member in a bag shape;
      said cylindrical net member forming a pair of ear members between said slits, such that the cylindrical net member is opened at a notched space formed by the slits, the cylindrical net member adapted to be held by sandwiching the ear members between a toilet stool and a toilet seat;
   a sleeve member having a cylindrical shape in which the capsule-type medical device collector can be inserted;
   gloves and a mask for collecting the capsule-type medical device; and
   a collection bag for housing the capsule-type medical device collector, the sleeve member, the gloves, and the mask.

2. The capsule-type medical device collecting kit according to claim 1, wherein the capsule-type medical device collector further includes handle members provided at one end of the cylindrical net member so as to face each other.

3. The capsule-type medical device collecting kit according to claim 2, wherein the handle member is provided at an end of each of the ear members.

4. The capsule-type medical device collecting kit, according to claim 1, further comprising:
   a housing bag for housing the capsule-type medical device that has been collected by the capsule-type medical device collector; and
   a kitbag for housing a manual in which a procedure for collecting the capsule-type medical device is written.

5. The capsule-type medical device collecting kit according to claim 1, wherein
   the collection bag is formed to be not transparent so that the dirty things housed therein cannot be seen from outside.

6. The capsule-type medical device collecting kit according to claim 5, wherein the collection bag is formed to be not transparent by aluminum evaporation.

7. The capsule-type medical device collecting kit according to claim 5, wherein the collection bag comprises a zipper member for closing an opening of the collection bag.

* * * * *